(12) United States Patent
Jain et al.

(10) Patent No.: US 12,084,601 B2
(45) Date of Patent: Sep. 10, 2024

(54) PACKAGING PATCHES HAVING DISINFECTING SEALING LAYER

(71) Applicant: AMCOR FLEXIBLES NORTH AMERICA, INC., Neenah, WI (US)

(72) Inventors: Rishabh Jain, Appleton, WI (US); Claire E. Kalb, Minneapolis, MN (US)

(73) Assignee: AMCOR FLEXIBLES NORTH AMERICA, INC., Neenah, WI (US)

( * ) Notice: Subject to any disclaimer, the term of this patent is extended or adjusted under 35 U.S.C. 154(b) by 512 days.

(21) Appl. No.: 16/957,231

(22) PCT Filed: Dec. 28, 2017

(86) PCT No.: PCT/US2017/068784
§ 371 (c)(1),
(2) Date: Jun. 23, 2020

(87) PCT Pub. No.: WO2019/132934
PCT Pub. Date: Jul. 4, 2019

(65) Prior Publication Data
US 2021/0002515 A1 Jan. 7, 2021

(51) Int. Cl.
*C09J 7/24* (2018.01)
*B32B 27/06* (2006.01)
(Continued)

(52) U.S. Cl.
CPC ............. *C09J 7/243* (2018.01); *B32B 27/06* (2013.01); *B32B 27/12* (2013.01); *B32B 27/30* (2013.01);
(Continued)

(58) Field of Classification Search
CPC ............. Y10T 428/13; Y10T 428/1303; Y10T 428/1307; Y10T 428/1334;
(Continued)

(56) References Cited

U.S. PATENT DOCUMENTS

| 4,585,482 A | * | 4/1986 | Tice | ............. A01N 25/28 424/665 |
| 5,631,300 A | | 5/1997 | Wellinghoff | |

(Continued)

FOREIGN PATENT DOCUMENTS

| WO | 2005041660 A1 | 5/2005 |
| WO | 2010045280 A2 | 4/2010 |

(Continued)

OTHER PUBLICATIONS

Machine translation (Espacenet) of WO 2016/088387 A1. Translated Nov. 17, 2022. (Year: 2022).*

*Primary Examiner* — Maria V Ewald
*Assistant Examiner* — Ethan A. Utt

(57) ABSTRACT

A package includes a patch and a packaging film. The patch comprises a support and a sealing layer comprising chlorite ions. The support is permeable to chlorine dioxide. The packaging film has an inner surface defining at least a portion of an interior space of the package for housing an article. The packaging film is substantially impermeable to chlorine dioxide and is transparent to ultraviolet light. The patch is affixed to the inner surface of the packaging film by the sealing layer. Chlorine dioxide may be generated by subjecting the package to ultraviolet (UV) light such that the UV light reaches the sealing layer of the patch to convert the chlorite ions to chlorine dioxide.

19 Claims, 6 Drawing Sheets

(51) Int. Cl.
   *B32B 27/12* (2006.01)
   *B32B 27/30* (2006.01)
   *C09J 7/35* (2018.01)
   *C09J 7/38* (2018.01)

(52) U.S. Cl.
   CPC .................. *C09J 7/35* (2018.01); *C09J 7/381* (2018.01); *B32B 2250/03* (2013.01); *B32B 2250/04* (2013.01); *B32B 2250/05* (2013.01); *B32B 2307/71* (2013.01); *B32B 2307/7145* (2013.01); *B32B 2323/04* (2013.01); *B32B 2553/00* (2013.01); *B32B 2556/00* (2013.01)

(58) Field of Classification Search
   CPC ......... Y10T 428/1338; Y10T 428/1341; Y10T 428/1352; Y10T 428/1355; Y10T 428/1359; Y10T 428/1362; Y10T 428/1366; Y10T 428/1372; Y10T 428/1379; Y10T 428/1383; Y10T 428/1386; Y10T 428/28; Y10T 428/2804; Y10T 428/2813; Y10T 428/2817; Y10T 428/2826; Y10T 428/2848; Y10T 428/2852; Y10T 428/2857; Y10T 428/2878; Y10T 428/2883; Y10T 428/2891; B32B 7/02; B32B 7/04; B32B 7/12; B32B 33/00; B32B 2439/00; B32B 2439/40; B32B 2439/46; B32B 2439/70; B32B 2439/80; B32B 7/00; C09J 7/00; C09J 7/20; C09J 7/21; C09J 7/22; C09J 7/24; C09J 7/241; C09J 7/243; C09J 7/245; C09J 7/25; C09J 7/255; C09J 7/28; C09J 7/29; C09J 7/30; C09J 7/35; C09J 7/38; C09J 2301/00; C09J 2301/30; C09J 2301/302; C09J 2301/304; B65D 31/02; B65D 31/00
   USPC .... 428/34.1–34.3, 36.1, 343, 346, 347, 349, 428/354, 355 R, 356, 355 EN, 355 BL, 428/355 AC, 35.2–35.4, 35.7–36.2, 428/36.6–36.8, 36.4, 344; 383/105, 109, 383/113, 116, 119
   See application file for complete search history.

(56) References Cited

U.S. PATENT DOCUMENTS

| | | |
|---|---|---|
| 5,695,814 A | 12/1997 | Wellinghoff et al. |
| 5,965,264 A | 10/1999 | Barenberg et al. |
| 5,980,826 A | 11/1999 | Barenberg et al. |
| 6,767,509 B1 | 7/2004 | Griesbach et al. |
| 7,273,567 B1 | 9/2007 | Wellinghoff et al. |
| 7,449,194 B2 | 11/2008 | Lelah et al. |
| 7,695,692 B2 | 4/2010 | Sanderson |
| 8,012,554 B2 | 9/2011 | Shelley et al. |
| 8,079,998 B2 | 12/2011 | Hole et al. |
| 2005/0079124 A1* | 4/2005 | Sanderson ............ C01B 11/024 422/186 |
| 2005/0106121 A1* | 5/2005 | Hartman ................ C08K 3/015 424/661 |
| 2005/0106380 A1 | 5/2005 | Gray et al. |
| 2008/0026029 A1 | 1/2008 | Wellinghoff et al. |
| 2008/0299066 A1 | 12/2008 | Wellinghoff et al. |
| 2012/0164025 A1 | 6/2012 | Stockley, III et al. |
| 2013/0264226 A1* | 10/2013 | Prikril .................... B65B 55/18 53/425 |
| 2014/0087033 A1 | 3/2014 | McKedy |
| 2014/0311094 A1 | 10/2014 | Thompson et al. |
| 2017/0157904 A1 | 6/2017 | Abbott et al. |

FOREIGN PATENT DOCUMENTS

| | | | |
|---|---|---|---|
| WO | WO-2016020755 A2 * | 2/2016 | ............ A01N 25/04 |
| WO | 2016069864 A2 | 5/2016 | |
| WO | WO-2016088387 A1 * | 6/2016 | ............ A01N 25/22 |
| WO | 2017031345 A1 | 2/2017 | |
| WO | 2017031351 A1 | 2/2017 | |
| WO | WO-2017031349 A1 * | 2/2017 | ............ A23B 7/144 |

* cited by examiner

PACKAGING PATCHES HAVING DISINFECTING SEALING LAYER

FIELD

This disclosure relates generally to compositions, sheets, patches and packages having chlorite salts, providing for on-demand release of chlorine dioxide ($ClO_2$) gas, and methods for releasing chlorine dioxide gas from such compositions, sheets, patches and packages.

BACKGROUND

Packages may incorporate a source of chlorite ions that may be activated by ultraviolet light to release chlorine dioxide to deodorize or disinfect the contents of the package. The packages employ multilayer films that include the chlorite ions in a layer of the film. The film or films are sealed to define an interior of the package into which the chlorine dioxide may be released upon activation of the chlorite ions. If the concentration of generated chlorine dioxide remains sufficiently high for a sufficient time, the contents of the sealed packages may be sterilized. Once generated, the chlorine dioxide has been found to degrade spontaneously over time under ambient room light and temperature to various oxychlorine ions ($Cl^-$, $ClO^-$, $ClO_2^-$, $ClO_3^-$) following first order kinetics with a half-life between 2-3 hours depending on the initial $ClO_2$ concentration generated. It can take between 12 to 48 hours for the concentration of chlorine dioxide in the package to reach levels sufficiently low for the package to be safely opened.

Incorporation of a source of chlorite ions into a layer of a multilayer packaging film presents several challenges. For example, compounding or extruding sodium chlorite with a polymeric melt is challenging due to thermal degradation of sodium chlorite at processing temperatures greater than 180° C. which reduces the active ingredient in the final formulation. In addition, this presents a safety hazard due to the possibility of a thermal runaway event. This is because sodium chlorite decomposes in an exothermic reaction (at temperatures (T) above 180° C.) to sodium chlorate and sodium chloride which can lead to a rapid rise in temperature that in turn can lead to the exothermic breakdown of sodium chlorate (at T>250-300° C.) into sodium chloride and gaseous oxygen—which is a fire hazard. Because of the heat sensitivity of sodium chlorite, existing film structures and manufacturing specifications which often incorporate polymers having high processing temperatures (>180° C.) need to be re-engineered and designed to safely and viably incorporate the source of chlorite ions into a layer of the packaging films. In addition, printing on the exterior of a package made from above-referenced multilayer film may alter the amount of chlorine dioxide that may be released because the printing may block transmission of ultraviolet light to the chlorite-containing layer.

SUMMARY

This disclosure relates to, among other things, incorporation of a source of chlorite ions into a sealing layer of patches or sheets for forming patches. The patches having the sealing layer that includes the source of chlorite ions may be affixed to an inner surface of the package or surface of the film for forming the package. Chlorine dioxide is generated by exposing the sealing layer of the patches to ultraviolet light.

In various embodiments of the present disclosure, a film that may be in the form of, for example, a patch is described. The film has a support layer that is permeable to chlorine dioxide and defines a first major surface of the film. The film also comprises a sealing layer that includes chlorite ions. The sealing layer is in contact with the support layer and defines a second major surface of the film. The sealing layer is configured to affix the film to another structure, such as an inner surface of a package. Preferably, the support is opaque to ultraviolet light. The sealing layer may comprise any suitable sealing composition, such as a heat sealable polymeric composition, a pressure sensitive adhesive composition, or the like.

In various embodiments of the present disclosure, a package is described. The package includes the film in the form of the patch and includes a packaging film. The patch comprises the sealing layer comprising the chlorite ions. The packaging film has an inner surface defining at least a portion of an interior space of the package for housing an article. The packaging film is substantially impermeable to chlorine dioxide. The film in the form of the patch is affixed to the inner surface of the packaging film by the sealing layer. The portion of the film to which the package is affixed is transparent to ultraviolet light.

In various embodiments of the present disclosure, a method is described. The method comprises providing the package having the packaging film and the patch affixed to the inner surface of the packaging film. The patch comprises the support and the sealing layer containing the chlorite ions. The method further includes subjecting the package to ultraviolet light having a wavelength of about 254 nm (UV254) to generate chlorine dioxide from the chlorite ions in the sealing layer of the patch. The UV254 may be directed through the package towards the sealing layer of the patch. The method may further include subjecting the package to ultraviolet light having a wavelength in a range from about 300 nm to about 390 nm, such as about 365 nm (UV365), to accelerate the degradation of the generated chlorine dioxide. The ultraviolet light having the wavelength in a range from about 300 nm to about 390 nm may be directed through the package towards the support of the patch, which, if UV opaque, may prevent a substantial amount of the ultraviolet light having the wavelength in a range from about 300 nm to about 390 nm from reaching the sealing layer comprising the chlorite ions to prevent further generation of chlorine dioxide.

Various embodiments of the methods, compositions, sheets, patches and packages described herein provide one or more advantages relative to currently available or previously described methods, compositions, sheets, patches and packages that incorporate a source of chlorite ions for generating chlorine dioxide. For example, the patches may be applied to any existing packaging that is transparent to ultraviolet light and that is substantially impermeable to chlorine dioxide (e.g., includes a barrier layer). Accordingly, major redesigns and modifications to manufacturing specifications need not be undertaken to incorporate on-demand chlorine dioxide sterilization into packages. In addition, only a portion of the package to which the patch is applied needs to be transparent to ultraviolet light, leaving the rest of the package available for printing, labeling, or other modifications that may affect ultraviolet transparency. Further, applying patches to the package such that the sealing layer of the patch contacts the inner surface of the packaging film, prevents contact of articles stored in the package with the source of chlorite ions. The lack of contact between the source of chlorite ions and the article within the package may be beneficial for sensitive articles, such as electronic articles, articles for use in the medical field, or articles containing pharmaceuticals, for example.

In some preferred embodiments, a sealing composition to form the sealing layer is applied to the patch or the sheet for forming patches under ambient conditions or at temperatures substantially lower than those associated with thermal compounding or extruding. Accordingly, handling and manufacturing of the patches and associated packages may be safer than prior processes for incorporating chlorite ions that involve high temperature conditions. Further, reduced loss of chlorite ion may be realized as the thermally sensitive chlorite ions are subjected to lower temperature processing in some preferred embodiments described herein.

The use of patches that include an ultraviolet opaque structural layer allows for processes that accelerate the degradation of chlorine dioxide by applying a source of ultraviolet light having a wavelength in a range from about 300 nm to about 390 nm. The opaque patch can block the ultraviolet light from reaching the sealing layer comprising the chlorite ions if the light is applied in an appropriate direction. The ultraviolet light having a wavelength in a range from about 300 nm to about 390 nm can accelerate degradation of the chlorine dioxide without producing more chlorine dioxide if the source of chlorite ions is blocked from the ultraviolet light. Accordingly, the packages may be safely opened in substantially less time than previous processes that allow chlorine dioxide to spontaneously degrade under ambient conditions. For example, embodiments of the packages and processes described herein allow for a sterilization to safe package opening cycle time of about 4 to 6 hours, as opposed to 48 hours with previously available packages and methods.

Additional features and advantages of the subject matter of the present disclosure will be set forth in the detailed description which follows, and in part will be readily apparent to those skilled in the art from that description or recognized by practicing the subject matter of the present disclosure as described herein, including the detailed description which follows, the claims, as well as the appended drawings.

It is to be understood that both the foregoing general description and the following detailed description present embodiments of the subject matter of the present disclosure, and are intended to provide an overview or framework for understanding the nature and character of the subject matter of the present disclosure as it is claimed. The accompanying drawings are included to provide a further understanding of the subject matter of the present disclosure, and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative, and are not intended to limit the scope of the claims in any manner.

BRIEF DESCRIPTION OF THE DRAWINGS

The following detailed description of specific embodiments of the present disclosure can be best understood when read in conjunction with the following drawings, where like structure is indicated with like reference numerals.

Figure 1:
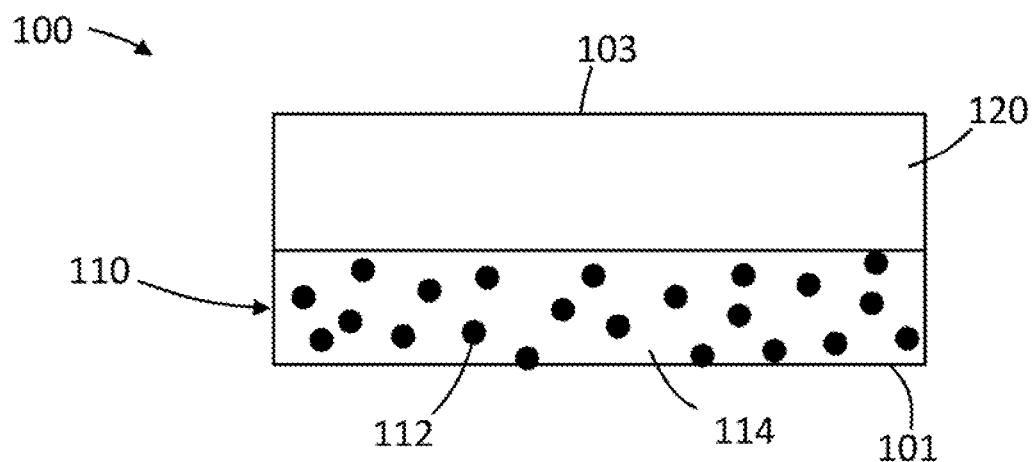
FIG. 1 is a schematic sectional view of an embodiment of a film, which may be in the form patch.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Reference will now be made in greater detail to various embodiments of the subject matter of the present disclosure, some embodiments of which are illustrated in the accompanying drawings.

This disclosure relates to, among other things, incorporation of a source of chlorite ion into a sealing layer of a patch or sheet for forming the patch. The patch may be affixed, via the sealing layer, to an inner surface of a package or a surface of a film for forming the package. The package may be exposed to ultraviolet light to generate chlorine dioxide from chlorite ions in the sealing layer of the patch.

The sealing layer of the patch may comprise any suitable amount of chlorite ion. The amount of chlorite ion in the sealing layer or composition is preferably sufficiently high to deodorize, disinfect, or sterilize an article disposed in the interior of the package to which the patch is affixed. The concentration of chlorite ion in the sealing layer may be varied depending on the thickness of the sealing layer, the surface area (length×width) of the patch used, and volume of the interior of the package, and the effect desired (such as deodorize, disinfect, or sterilize). Any suitable amount of chlorite ion may be included in the sealing layer or sealing composition to deodorize, disinfect, or sterilize the interior of a package and the contents of the package may vary depending on the volume of the interior of the package.

Any suitable source of chlorite ion may be included in the sealing layer or sealing composition. Typically, the source of chlorite ion is a chlorite salt. A "chlorite salt" as used herein is not limited to embodiments wherein the anion and cation form a solid crystal, but in fact encompass any form in which such salts are known to exist, including in aqueous or other solutions or dispersed within a polymeric matrix. In some embodiments, the cation of the chlorite salt is an organic cation, and in some embodiments the cation of the chlorate salt is inorganic. In some such embodiments, the chlorite salt is sodium chlorite, potassium chlorite, calcium chlorite, magnesium chlorite, lithium chlorite or ammonium chlorite. In some embodiments, the chlorite salt is sodium chlorite.

Typically, the sealing layer will comprise less than about 70% by weight of chlorite salt so that the sealing layer may maintain effective sealing properties. The sealing layer will typically comprise at least about 0.1% of by weight chlorite salt so that a sufficient amount of chlorine dioxide may be generated. The sealing may include any suitable amount of chlorite salt. The amount of chlorite salt can be varied to help control the amount of $ClO_2$ that is generated. In non-limiting examples, the weight percent of the chlorite salt is, for example, 0.1%, 1%, 5%, 10%, 15%, 20%, 25%, 30%, 35%, 40%, 45%, 50%, 55%, 60%, 65% or 70% of the weight of the sealing layer, or any amount in between. In some embodiments, the lower range of the weight of the chlorite salt may be, for example, 0.1%, 1%, 5%, 10%, 5%, 20%, 25%, 30%, 35%, 40%, 45%, 50%, 55%, 60%, or 65% of the weight of the sealing layer composition, while the upper range of the weight of the chlorite salt may be 15%, 20%, 25%, 30%, 35%, 40%, 45%, 50%, 55%, 60%, 65%, or 70% of the weight of the sealing layer composition. This disclosure encompasses all weight percentage ranges that are defined by any combination of these lower and upper bounds.

The patches or sheets for forming the patches may include any suitable sealing layer comprising chlorite ion. As used herein, a "sealing layer" is a layer comprising a composition configured to affix the patch to another structure, such as a surface of a package or packaging film, via fusion bonding or chemical bonding, such as adhesion. For example, the sealing layer may comprise a heat sealable polymeric composition, a cold seal adhesive, or a pressure sensitive adhesive.

In use, the sealing layer is an outermost layer of the patch or sheet for forming the patch. That is, the sealing layer forms one of the two major surfaces of the patch or sheet. In the case of a patch or sheet having a sealing layer comprising pressure sensitive adhesive, the patch or sheet may include a release liner prior to use. The pressure sensitive adhesive may be disposed between a support and the release liner. The release liner may be removed prior to affixing the patch to the packaging or packaging film.

The sealing layer may comprise any suitable cold seal adhesive. Cold seal adhesives possess the capability of forming a strong bond to themselves when pressure is applied, yet are also capable of being applied to a substrate and reeled as a dried film for storage without effecting such a bond. Accordingly, the adhesive must be sufficiently deformable to form a bond under the application of pressure alone, yet sufficiently hard to resist bonding to a substrate during storage. Such adhesives are well known and are used in a variety of applications including as envelope sealants and in food packaging where the application of heat to bond is undesirable.

Conventional cold seal adhesives combine a natural rubber elastomer, such as a latex, with a tackifier and other compounds. A cold seal adhesive may comprise, for example, 55-6) wt. % of a high ammonia content natural rubber latex emulsion, 30-40 wt. % of a styrene acrylate emulsion, and small amounts of wetting agents, latex stabilizers, thickeners, or other suitable additives. A suitable amount of a chlorite salt, such as an amount described above, may be added to a cold seal adhesive.

A number of synthetic alternatives to natural rubber-based cold seal adhesives have been developed and may be used. Examples includes those commercially available from Henkel, those described in European Published Patent Application Publication No. EP0338304A, and the like.

The seal layer may comprise any suitable pressure sensitive adhesive. A pressure sensitive adhesive is a material that holds two surfaces together solely by surface contact, which is achieved by slight initial external pressure. Pressure sensitive adhesives require no activation with water, solvent or heat, and firmly adhere to many dissimilar surfaces with minimal pressure.

Examples of suitable pressure sensitive adhesives include acrylate polymer pressure sensitive adhesives, rubber (either natural or synthetic thermoplastic elastomer) pressure sensitive adhesives, silicone pressure sensitive adhesives, and the like. The pressure sensitive adhesives may comprise a tackifier such as a rosin ester, as appropriate. The pressure sensitive adhesives may be a solvent-based pressure sensitive adhesive in which a rubber or acrylic is dissolved in a solvent and then coated on a support, such as a support film. The solvent may be evaporated leaving a dry sticky pressure sensitive adhesive. The pressure sensitive adhesive may be an emulsion-based pressure sensitive adhesive in which an acrylic polymer and other additives are dispersed in water and coated on a support. The water may be evaporated leaving a dry sticky pressure sensitive adhesive. The pressure sensitive adhesive may be a hot-melt pressure sensitive adhesive in which a thermoplastic rubber or elastomer, tackifying resin and diluent, such as a plasticizer, is heated until it is fluid and then coated on a support and cooled.

Any suitable amount of a chlorite salt may be added to the pressure sensitive adhesive composition applied to a support to achieve a pressure sensitive adhesive layer having a suitable chlorite ion concentration. Preferably, the pressure sensitive adhesive is formed by a process that does not involve elevated temperature, such as temperatures above 320° F., due to the temperature sensitivity of chlorite ions. Accordingly, hot-melt pressure sensitive adhesives are less preferred. While less preferred, hot-melt pressure sensitive adhesives may be employed.

The seal layer may comprise any suitable heat seal layer. The heat seal layer may comprise any suitable sealing composition, such as a heat sealable polymeric composition. In some embodiments, the heat sealable polymeric composition comprises a polyolefin. "Polyolefin" is used herein broadly to include polymers such as polyethylene, ethylene-alpha olefin copolymers (EAO), polypropylene, polybutene, ethylene copolymers having a majority amount by weight of ethylene polymerized with a lesser amount of a co-monomer such as vinyl acetate, and other polymeric resins falling in the "olefin" family classification. Polyolefins may be made by a variety of processes well known in the art including batch and continuous processes using single, staged or sequential reactors, slurry, solution and fluidized bed processes and one or more catalysts including for example, heterogeneous and homogeneous systems and Ziegler, Phillips, metallocene, single site and constrained geometry catalysts to produce polymers having different combinations of properties. Such polymers may be highly branched or substantially linear and the branching, dispersity and average molecular weight and may vary depending upon the parameters and processes chosen for their manufacture in accordance with the teachings of the polymer arts.

In some embodiments, the heat seal layer comprises a cyclic olefin copolymer (COC), such as an ethylene norbornene copolymer. In some embodiments, the heat seal layer comprises one or more of polyethylene, ethylene vinyl acetate, ethylene alpha-olefins, or polypropylene. In some embodiments, the sealing layer comprises a blend of polymers to obtain suitable or desired properties.

The chlorite ion may be applied to a composition for forming the heat seal layer in any suitable manner. In some embodiments, the chlorite ion is mixed with the heat sealable polymeric composition in a suitable concentration and the mixture is extruded to form the heat seal layer. Preferably, the heat seal layer is formed in a manner that does not require elevated temperatures. For example, the heat seal layer may be formed from a polyolefin dispersion to which the chlorite salt may be added. An example of a suitable polyolefin dispersion is the Dow HYPOD™ polyolefin dispersion, such as Dow's HYPOD™ 8501, 8502, 8503, 1001 or 1000.

Regardless of the composition or type of the sealing layer and the process for applying the sealing layer, the sealing layer may have any suitable thickness. In some embodiments, the resulting sealing layer of the patch or a sheet for forming the patch has a thickness from about 0.1 mils to about 1 mil, such as from about 0.25 mils to about 0.75 mils. When the coating is applied to, for example, non-woven materials the coating may be applied at any suitable weight. For example, the dry coating weight may be from about 1 to about 15 pounds per ream, such as from about 3 to about 11 pounds per ream.

Preferably the sealing layer is transparent to ultraviolet radiation (e.g., at least 10% of ultraviolet light can be transmitted through the sealing layer).

The sealing layer may be applied to the support in any suitable manner. For example, the sealing layer and the support may be co-extruded to form a film that may form the patch or a sheet for forming the patch. The sealing layer may be coated on, sprayed on, rolled on, printed on, adhered to or otherwise applied to the support. The sealing layer may be disposed across an entire surface of the support or across one or more portions of the surface of the support. In some embodiments, the sealing layer is applied to the entire surface of the support using a gravure or air knife coating process.

The sealing layer may comprise more than one layer provided that chlorite ions are present in at least one layer. The layer containing the chlorite ions and any layers between the chlorite ion containing layer and the surface of the sealing layer must be transparent to ultraviolet radiation.

The sealing layer may be applied to any suitable support to form the patch or the sheet for forming the patch. It will be understood that the patch or the sheet for forming the patch are "films." As used herein, a "film" is thin structure having a length and width substantially greater than its depth or thickness. Typically, the length and width of a film is at least 100 times greater than the thickness of the film, such as at least 1000 times greater than the thickness of the film. Accordingly, the term "film" may include paper, cloth, non-woven materials, as well as polymeric films.

The film forming the patch or the sheet for forming the patch may have any suitable support. The support is permeable to chlorine dioxide. The support may be formed from material that is permeable to chlorine dioxide or may be modified to be permeable to chlorine dioxide. For example, a support that is not initially permeable to chlorine dioxide may be made permeable by perforating the support. Accordingly, a wide variety of materials may be used to form the support.

Permeability to oxygen may serve as a proxy for permeability to chlorine dioxide. In some embodiments, the support will have an oxygen transmission rate (O2TR) of at least 100 cm3/m2/24 hours at 1 atmosphere and 23° C., such as least 250 cm3/m2 per 24 hours at 1 atmosphere. Oxygen transmission rate (O2TR) may be determined by any suitable method. For example, oxygen transmission rate may be determined according to ASTM D3985.

The support may be formed from fibers or material in any other suitable form. In some embodiments, the support comprises a nonwoven material. In some embodiments, the nonwoven material comprises spun polyolefin fibers, polyesters fibers, polyamide fibers, or the like. In some embodiments, the support comprises polyethylene fibers. In some embodiments, the polyethylene fibers are high-density polyethylene fibers. In some embodiments, the high-density polyethylene fibers are flash spun high-density polyethylene fibers. One suitable example of flash spun high-density polypropylene fibers is Dupont's TYVEK® sheet material.

In some embodiments, the support is paper or cloth. In some embodiments, the support is a polymeric film that is permeable to chlorine dioxide or that is perforated or otherwise modified to be permeable to chlorine dioxide.

The film that forms the patch or sheet may comprise, consist essentially of, or consist of the support and the sealing layer comprising the chlorite ions. The support may comprise one or more layers, provided that chlorine dioxide is permeable through each layer.

The film may be in the form of a sheet from which one or more patches may be formed. For example, the sheet may be punched or cut to form the patches. As used herein, a "sheet" includes a roll of the film.

Preferably the support is opaque to ultraviolet radiation, particularly ultraviolet light having a wavelength in a range from about 200 nm to about 390 nm. For example, the supports blocks transmission of more than 90% or more of ultraviolet light. In some embodiments, the support blocks transmission of 95% or more or ultraviolet light. As described in more detail below, having an ultraviolet opaque support may be helpful in methods for accelerating the breakdown of chlorine dioxide to reduce the amount of time from activation of chlorite ions to safely opening a package that includes a patch having a sealing layer containing the chlorite ions.

Examples of materials that may be ultraviolet opaque and that may be used to form the support include polymers with aromatic moieties that absorb UV254 nm light such as polyesters, aromatic polyamides, polystyrene and the like. Flash spun high-density polyethylene fibers, such as Dupont's TYVEK®, may be ultraviolet opaque.

Any suitable package may include a patch having a sealing layer comprising chlorite ions. The package may include a packaging film having an inner surface defining at least a portion of an interior space of the package for housing an article. The packaging film is substantially impermeable to chlorine dioxide. At least the portion of the package to which the patch is affixed is transparent to ultraviolet light. The packaging film may comprise a single or multilayer film. The patch is affixed to the inner surface of the packaging film. The packaging film may be flexible or rigid, depending on the type of package being formed. The package may be in the form of a bag, pouch, or other suitable container. The packaging film to which the patch is affixed may be, for example, a side of the bag, pouch or container, or may be a lid for a container such as a thermoformed tray. In some embodiments, the patch is affixed to a thermoformed tray or other suitable container formed from a packaging film.

The process for affixing the patch to the surface of the packaging film will depend on the sealing layer of the patch. For example, if the sealing layer is a heat seal layer, the patch may be heat sealed to the packaging film. If the sealing layer comprises a pressure sensitive adhesive, the patch may be pressed against the packaging film. If the sealing layer comprises a cold seal adhesive, the patch may be pressed against a surface of the packaging film comprising a cold seal layer. The cold seal layer may be applied to the entire surface of the packaging film or to any suitable portion for affixing the patch comprising a cold seal adhesive.

The packaging film may comprise any suitable number of layers. For example, the packaging film may comprise one or more of a sealing layer, a barrier layer, an abuse-resistant outer layer, an intermediate layer, a tie layer, and the like.

The packaging film may comprise any suitable sealing layer, such as a sealing layer described above regarding the patch or sheet for forming the patch. Preferably, the packaging film comprises a heat seal layer, and the film is heat sealed to, for example, itself, another film, or a container to form a sealed package. Heat sealing may form a hermetic seal. The patch may be affixed to the packaging film at any suitable time prior to final sealing of the package. The sealing layer of the packaging film may have easy-peel functionality. If the packaging film comprises a heat seal layer to form the package, the patch is preferably affixed to a sheet of the packaging film prior to the film being even partially sealed to form the package.

A sealing layer of the packaging film may have any suitable thickness. In some embodiments, a sealing layer of the packaging film has a thickness of 2.5 micrometers or greater, such as 3 micrometers or greater. In some embodiments, the sealing layer of the packaging film has a thickness of 25 micrometers or less.

The packaging film is preferably non-permeable to appreciable amounts of chlorine dioxide. For example, the packaging film may have an oxygen transmission rate ($O_2TR$) of less than 150 $cm^3/m^2/24$ hours at 1 atmosphere and 23° C., such as less than 100 $cm^3/m^2$ per 24 hours at 1 atmosphere. In some embodiments, the packaging film has an $O_2TR$ of less than 10 $cm/m^2$ per 24 hours at 1 atmosphere and 23° C. such as less than 1 $cm^3/m^2$ per 24 hours at 1 atmosphere and 23° C. Oxygen transmission rate ($O_2TR$) may be determined by any suitable method. For example, oxygen transmission rate may be determined according to ASTM D3985.

To achieve such low permeabilities, the packaging film may include one or more barrier layers. If included, a barrier layer preferably functions both as a gas barrier layer, and as a moisture barrier layer, although these functions may be provided by separate layers. The barrier layer is preferably a core layer positioned between and protected by surface layers. For example, a barrier layer can be in contact with a first surface layer and an adhesive layer or may be sandwiched between two tie layers, two surface layers, or a tie layer and a surface layer.

A barrier layer may comprise any suitable material and may be any suitable thickness. A gas barrier layer can comprise polyvinyl alcohol (PVOH), ethylene vinyl alcohol (EVOH), polyvinylidene chloride (PVDC), polyamide, polyester, polyalkylene carbonate, polyacrylonitrile, a nanocomposite, or the like. Preferably, the barrier layer is transparent to ultraviolet light. The thicknesses of the barrier layers may be selected to provide the desired combination of the performance properties sought e.g. with respect to oxygen permeability, water vapor permeability, delamination resistance, etc.

A bulk layer may be provided to provide additional functionality such as stiffness or heat sealability or to improve machinability, cost, flexibility, barrier properties, etc. Preferred bulk layers comprise one or more polyolefins such as polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the olefin family classification. The bulk layer may be of any suitable thickness or may even be omitted for use in certain applications.

The packaging film may include an abuse resistant outer layer. Since the outer layer is seen by the user/consumer, in both monolayer and multilayer embodiments, the exterior surface of the packaging film preferably has desirable optical properties and may have high gloss. Also, it preferably withstands contact with sharp objects and provides abrasion resistance, and for these reasons it is often termed the abuse resistant layer. This exterior abuse-resistant layer may or may not also be used as a heat sealable layer and thus may comprise one or more suitable polymers such as polyethylene or polypropylene. As the exterior surface layer of the film, this layer most often is also the exterior layer of any package, such as a bag, a pouch or other container, made from the packaging film, and is therefore subject to handling and abuse e.g. from equipment during packaging, and from rubbing against other packages and shipping containers and storage shelves during transport and storage.

The exterior surface layer should be easy to machine (i.e. be easy to feed through and be manipulated by machines e.g. for conveying, packaging, printing or as part of the film or bag manufacturing process). Suitable stiffness, flexibility, flex crack resistance, modulus, tensile strength, coefficient of friction, printability, and optical properties are also frequently designed into exterior layers by suitable choice of materials. This layer may also be chosen to have characteristics suitable for creating desired heat seals which may be resistance to burn through e.g. by impulse sealers or may be used as a heat sealing surface in certain package embodiments e.g. using overlap seals.

Suitable exterior surface layers may comprise: polyamide, polyolelin, cast or oriented nylon, polypropylene, or copolymers, or blends thereof. Oriented films of this or any other layer may be either uni-axially or bi-axially oriented. The exterior layer thickness is typically 0.5 to 2.0 mils. Thinner layers may be less effective for abuse resistance, however thicker layers, though more expensive, may advantageously be used to produce films having unique highly desirable puncture resistance and/or abuse resistance properties.

A packaging film described herein may include an intermediate layer. An intermediate layer is any layer between the exterior layer and the interior layer and may include oxygen barrier layers, tie layers or layers having functional attributes useful for the film structure or its intended uses. Intermediate layers may be used to improve, impart or otherwise modify a multitude of characteristics: e.g. printability for trap printed structures, machinability, tensile properties, flexibility, stiffness, modulus, designed delamination, easy opening features, tear properties, strength, elongation, optical, moisture barrier, oxygen or other gas barrier, radiation selection or barrier e.g. to ultraviolet wavelengths, etc. Suitable intermediate layers may include: adhesives, adhesive polymers, paper, oriented polyester, amorphous polyester, polyamide, polyolefin, nylon, polypropylene, or copolymers, or blends thereof. Suitable polyolefins may include: polyethylene, ethylene-alpha olefin copolymers (EAO), polypropylene, polybutene, ethylene copolymers having a majority amount by weight of ethylene polymerized with a lesser amount of a comonomer such as vinyl acetate, and other polymeric resins falling in the "olefin" family classification, LDPE, HDPE, LLDPE, EAO, ionomer, ethylene methacrylic acid (EMA), ethylene acrylic acid (EAA), modified polyolefins e.g. anhydride grafted ethylene polymers, etc.

A packaging film as described herein may comprise one or more adhesive layers, also known in the art as "tie layers," which can be selected to promote the adherence of adjacent layers to one another in a multilayer film and prevent undesirable delamination. A multifunctional layer is preferably formulated to aid in the adherence of one layer to another layer without the need of using separate adhesives by virtue of the compatibility of the materials in that layer to the first and second layers. In some embodiments, adhesive layers comprise materials found in both the first and second layers. The adhesive layer may suitably be less than 10% and preferably between 2% and 10% of the overall thickness of the multilayer film.

Multilayer films can comprise any suitable number of tie or adhesive layers of any suitable composition. Various adhesive layers are formulated and positioned to provide a desired level of adhesive between specific layers of the film according to the composition of the layers contacted by the tie layers.

The interior, exterior, intermediate or tie layers may be formed of any suitable thermoplastic materials, for example, polyamides, polystyrenes, styrenic copolymers e.g. styrene-butadiene copolymer, polyolefins, and in particular members of the polyethylene family such as LLDPE, VLDPE, HDPE, LDPE, COC, ethylene vinyl ester copolymer or ethylene alkyl acrylate copolymer, polypropylenes, ethylene-propylene copolymers, ionomers, polybutylenes, alpha-olefin polymers, polyesters, polyurethanes, polyacrylamides, anhydride-modified polymers, acrylate-modified polymers, polylactic acid polymers, or various blends of two or more of these materials.

Various additives may be included in the polymers utilized in one or more of the exterior, interior and intermediate or tie layers of packaging comprising the same. For example, a layer may be coated with an anti-block powder. Also, conventional anti-oxidants, anti-block additives, polymeric plasticizers, acid, moisture or gas (such as oxygen) scavengers, slip agents, colorants, dyes, pigments, organoleptic agents may be added to one or more film layers of the film or it may be free from such added ingredients.

The layers, components, additives, and the like of the packaging film may be selected such that the packaging film is transparent to ultraviolet radiation, particularly radiation having a wavelength in a range from about 250 nm to about 370 nm.

The packaging films described herein may be made in any suitable manner, such as by conventional processes. Processes to produce flexible films may include e.g. cast or blown film processes, or extruding processes.

A packaging film described herein may have any suitable thickness. In some embodiments, the packaging film has a total thickness of less than about 50 mils, more preferably the film has a total thickness of from about 1.0 to 10 mils (25-250 microns), such as from about 1 to 5 mils, or from about 2 to 3.5 mils. For example, entire multilayer films or any single layer of a multilayer film can have any suitable thicknesses, including 1, 2, 3, 4, 5, 6, 7, 8, 9, 10 or 50 mis, or any increment of 0.1 or 0.01 mil there between.

In some embodiments, the packaging films areas thick as 50 mils (1270 microns) or higher, or as thin as 1 mil (25.4 microns) or less. In various embodiments, the packaging films have a thickness of between about 2-4 mil (51-102 microns).

Packages may be formed from films in any suitable manner. In some embodiments, the packages are formed by heat sealing a film to itself or another suitable film. In some embodiments, packages such as pouches are thermoformed from the films. In some embodiments, films are heat sealed across an opening of a container. The packaging films are preferably sealed to form the package after the patch comprising the sealing layer containing the chlorite ions is affixed to the packaging film. Prior to final sealing, an article may be placed in the package. Accordingly, once the packaging film is sealed to form the final package, the article is disposed within the interior space of the package.

Any suitable article may be disposed in a package described herein. Examples of suitable articles include food products, pharmaceutical products, laboratory devices, and medical devices. Examples of suitable produce that may be packaged in a film described herein include lettuce, grapes, spinach, or the like. Any suitable medical device may be disposed in a package comprising the multilayer packaging film described herein. For example, catheters such as balloon dilatation catheters, guide catheters, aspiration catheters, and diagnostic catheters; vacutainers; yankauers; enteral feeding kits; dressing gowns and drapes; coronary stents; surgical tools and equipment, sensors or other electronic medical devices, various forms of endoscopes including capsule endoscopes; or the like may be disposed within a sealed package as described herein.

Chlorine dioxide may be generated in the interior of a packages that include a patch having a sealing layer comprising a source of chlorite ions affixed to an inner surface of a packaging film in any suitable manner. For example, ultraviolet light may be directed through the packaging film towards the sealing layer of the patch to generate chlorine dioxide gas from the chlorite ions. The chlorine dioxide gas may permeate through the support of the patch to the interior of the package.

Generation of chlorine dioxide from the chlorite ions may be enhanced with moisture. The packages may be exposed to moisture before, during, or after the packages are subjected to ultraviolet light. In some embodiments, the step of exposing the package to moisture is performed by contacting the package with a humidified gas comprising water vapor. In some such embodiments, the humidified gas is heated above room temperature. In some such embodiments, the humidified gas includes steam. In some embodiments, ambient humidity may be used. In some embodiments, the water vapor is provided by the contents of the package or an article stored in the package. For example, if the article stored in the package is a food product such as produce, the article may provide sufficient moisture to enhance the generation of chlorine dioxide by the ultraviolet light. In some embodiments, the water may be applied to the patch before, during, or after the patch is affixed to the package or the packing film for forming the package. In some embodiments, moisture may be supplied by placing a wetted component in the package. For example, wetted tissue paper or other suitable wetted substrate may be placed in the package to supply moisture. Additional information regarding application of moisture and UV light to generate chlorine dioxide from compositions or packages including chlorite ions is disclosed in, for example, PCT patent application publication no. WO 2017/031345, which is hereby incorporated herein by reference in its entirety to the extent that it does not conflict with the disclosure presented herein.

The ultraviolet light may be directed towards the sealing layer of the patch for a sufficient time to produce an effective amount of chlorine dioxide release within the interior space of the sealed package. As used herein, release of an "effective amount" of chlorine dioxide ($ClO_2$) gas means that the amount of the $ClO_2$ gas released is effective to accomplish its intended effect. For example, the amount of chlorine dioxide gas released may be effective to disinfect or deodorize, or disinfect and deodorize the interior of the package and the article in the package. The amount of chlorine dioxide gas released may be effective to sterilize the interior of the package and the article in the package.

As used herein, "deodorize" means to remove or conceal an unpleasant smell. In many cases, the unpleasant smell may be caused by odor-causing bacteria, and killing of the bacteria may have a deodorizing effect. A composition described herein may release any suitable amount of $ClO_2$ gas to deodorize an article stored in the package, such as a food product, which may be, for example, produce. For example, a film may release at least 2 parts per million (ppm) $ClO_2$ into an interior volume of the package. Typically, release of at least 10 ppm $ClO_2$ gas is sufficient to deodorize produce. The concentration of chlorine dioxide may increase over time if the package is sealed, as additional chlorine dioxide is released. The amount of $ClO_2$ gas needed to effectively deodorize an article stored in the package will depend, in part, on the nature of the article. In addition, the time that the article is exposed to $ClO_2$ gas will affect the ability of the $ClO_2$ gas to deodorize the article. In some embodiments, an amount of $ClO_2$ gas is released for a time sufficient to expose the article to at least 2 ppm·hours of $ClO_2$ gas to deodorize the article. For example, an amount of chlorine dioxide to result in at least 10 ppm·hours of $ClO_2$ gas, or at least 20 ppm·hours of $ClO_2$ gas may be released to deodorize the article.

As used herein, "disinfect" means to reduce the number of living bacteria. To determine whether an article, such as a food product, which may be produce, is disinfected, the article that has undergone a disinfecting treatment, such as exposure to $ClO_2$ gas, can be compared to control article that has not undergone the disinfecting treatment to determine whether bacterial burden has been reduced; and, if so, the article will be considered to have been disinfected. Alternatively, the bacterial burden of an article, such as produce, may be compared before and after treatment to determine whether the article has been disinfected. Any suitable amount of $ClO_2$ gas may be released to the interior of the package to disinfect an article disposed within the interior of package. For example, at least 10 parts per million (ppm) $ClO_2$ gas may be released into an interior volume of the package. In some embodiments, at least 50 ppm or greater $ClO_2$ gas is released into the interior of the package to disinfect the article. The amount of $ClO_2$ gas needed to effectively disinfect produce will depend, in part, on the nature of the article. In addition, the time that the article is exposed to $ClO_2$ gas will affect the ability of the $ClO_2$ gas to disinfect the article. In some embodiments, exposure to ultraviolet radiation releases an amount of $ClO_2$ gas to effectively expose the article to 100 ppm·hours or greater of $ClO_2$ gas to disinfect the article. For example, an amount of chlorine dioxide to result in at least 150 ppm·hours or more of $ClO_2$ gas, or at least 200 ppm·hours of $ClO_2$ gas, may be released to disinfect the article.

As used herein "sterilize" means to make free from bacteria or other living organisms. Any suitable amount of $ClO_2$ gas may be released to sterilize an article, such as a medical device, disposed within an interior of the package. For example, at least 200 parts per million (ppm) $ClO_2$ gas may be released into an interior volume of package. In some embodiments, at least 500 ppm $ClO_2$ gas is released into the interior of the package to sterilize the article stored in the interior of the package. The amount of $ClO_2$ gas needed to effectively sterilize an article will depend, in part, on the nature of the article. In addition, the time that the article is exposed to $ClO_2$ gas will affect the ability of the $ClO_2$ gas to sterilize the article. In some embodiments, an amount of $ClO_2$ gas is released for a time sufficient to expose the article to at least 360 ppm·hours of $ClO_2$ gas to sterilize the article. For example, an amount of chlorine dioxide may be released for a time sufficient to expose the article to at least 1000 ppm·hours of $ClO_2$ gas, or at least 2000 ppm·hours of $ClO_2$ gas, to sterilize the article.

As described above, chlorine dioxide may be generated in the interior of the package by directing ultraviolet light through the packaging film towards the sealing layer of the patch to generate chlorine dioxide gas from the chlorite ions in the sealing layer of the patch. The ultraviolet light may be directed towards the sealing layer of the patch for a sufficient time to produce an effective amount of chlorine dioxide release within the interior space of the sealed package. In some embodiments, the ultraviolet light has a wavelength in the range of about 200 nm to 400 nm. In some such embodiments, the ultraviolet light has a wavelength in the range of about 230 nm to 320 nm. In some such embodiments, the ultraviolet light has a wavelength in the range of about 240 nm to 280 nm. Preferably, the ultraviolet light includes light having a wavelength of about 254 nm. The ultraviolet light may be a broad-spectrum light or a narrow-spectrum light. The source of UV light may be broad-spectrum or narrow-spectrum. In some embodiments, a broad-spectrum source is employed with a narrow spectrum filter. For example, a filter that allows light having a wavelength of about 254 nm may be used.

In some embodiments, the package is exposed to ultraviolet light for a period of time that is greater than 10 milliseconds. In some such embodiments, the package is exposed to ultraviolet light for a period of time that is greater than 10 seconds. In some such embodiments, the package is exposed to ultraviolet light for a period of time that is greater than 10 minutes. The amount of time that the package is exposed to ultraviolet light may depend on the intensity of the UV source, the distance of the UV source, and the desired level of chlorine dioxide.

In some embodiments, the step of exposing the composition to ultraviolet light may be repeated one or more times to generate chlorine dioxide gas.

Once a sufficient amount of chlorine dioxide has been generated and the chlorine dioxide has been present for a sufficient amount of time, the package may be exposed to ultraviolet light to accelerate the degradation of the chlorine dioxide. The ultraviolet light applied to accelerate the degradation of the chlorine dioxide may be a broad-spectrum light or a narrow-spectrum light. The source of UV light may be broad-spectrum or narrow-spectrum. In some embodiments, a broad-spectrum source is employed with a narrow spectrum filter. For example, a filter that allows light having a wavelength of about 312 nm or about 365 nm may be used. Regardless of whether the light applied has a broad spectrum or a narrow spectrum, the ultraviolet light for accelerating the degradation of the chlorine dioxide preferably has a wavelength that falls within a range from about 300 nm to about 390 nm. In some embodiments, the ultraviolet light has a wavelength range of about 365 nm+/−70 nm. In some preferred embodiments, the ultraviolet light includes a wavelength of about 312 nm or of about 365 nm. Preferably, the ultraviolet light includes a wavelength of about 365 nm.

While ultraviolet light having a wavelength that falls within a range from about 300 nm to about 390 nm will accelerate the degradation of chlorine dioxide, it will also generate chlorine dioxide from chlorite ions. Accordingly, a substantial portion of the ultraviolet light having a wavelength in a range from about 300 nm to about 390 nm is preferably blocked from reaching the sealing layer of the patch that contains the chlorite ions. This may be accomplished if the patch comprises an ultraviolet opaque support and if the ultraviolet light is directed towards the package from a side opposite the side to which the patch is affixed. In this manner, the opaque support layer of the patch will be exposed to the ultraviolet light, and the opaque support layer will prevent a substantial amount of the ultraviolet light from reaching the sealing layer comprising the chlorite ions. Preferably the support is opaque to ultraviolet light having a wavelength of about 365 nm, is opaque to ultraviolet light having a wavelength of about 312 nm, or is opaque to ultraviolet light having a wavelength in a range from about 300 nm to about 390 run.

The package may be exposed to the ultraviolet light having a wavelength in a range from about 300 nm to about 390 nm for any suitable amount of time. The amount of time may depend on the concentration of the chlorine dioxide in the interior package, the intensity of the ultraviolet light applied, and the like. For example, if the initial chlorine dioxide concentration in the package is about 500 ppm, the package may be exposed to the ultraviolet light having a wavelength of about 365 nm for a longer time than if the initial chlorine dioxide concentration is 10 ppm.

Preferably, the chlorine dioxide concentration is reduced to less than 0.5 ppm prior to the package being opened. In some embodiments, the chlorine dioxide concentration in the package is reduced to less than 0.5 ppm prior within about 24 hours following sterilization of the article in the package by the chlorine dioxide. In some embodiments, the chlorine dioxide concentration in the package is reduced to less than 0.5 ppm prior within about 12 hours following sterilization of the article in the package by the chlorine dioxide.

In some embodiments, the chlorine dioxide concentration in the package is reduced to less than 0.5 ppm prior within about 4 hours to 6 hours following sterilization of the article in the package by the chlorine dioxide. Such embodiments are somewhat comparable to cycle times required for sterilization by autoclaving.

In the drawings, various embodiments of patches, packaging films, packages, and methods are illustrated.

Referring now to FIG. 1, a schematic sectional view of a film 100 is shown. The film 100 has a first major surface 101 and a second major surface 103 and include a sealing layer 110 and a support layer 120. The sealing layer 110 comprises chlorite ions 112 and a sealing polymer or polymer-based formulation 114. The sealing layer 110 is in contact with the support 120. The support 120 is permeable to chlorine dioxide and is preferably opaque to ultraviolet radiation. If the support 120 is formed from material that is not permeable to chlorine dioxide, the support 120 may be made permeable by, for example, perforation.

The sealing layer 110 may be applied to the support 120 in any suitable manner to form the film. Preferably, the process for applying the sealing layer 110 to the support layer 120 is performed at temperatures substantially lower that those typically associated with extrusion due to the heat sensitivity of the chlorite ions 112. Preferably, the sealing layer 110 is applied to the support layer 120 at room temperature.

The film 100 may be in the form of a patch or a sheet, such as a roll of film, from which a patch may be formed.

Figure 2:
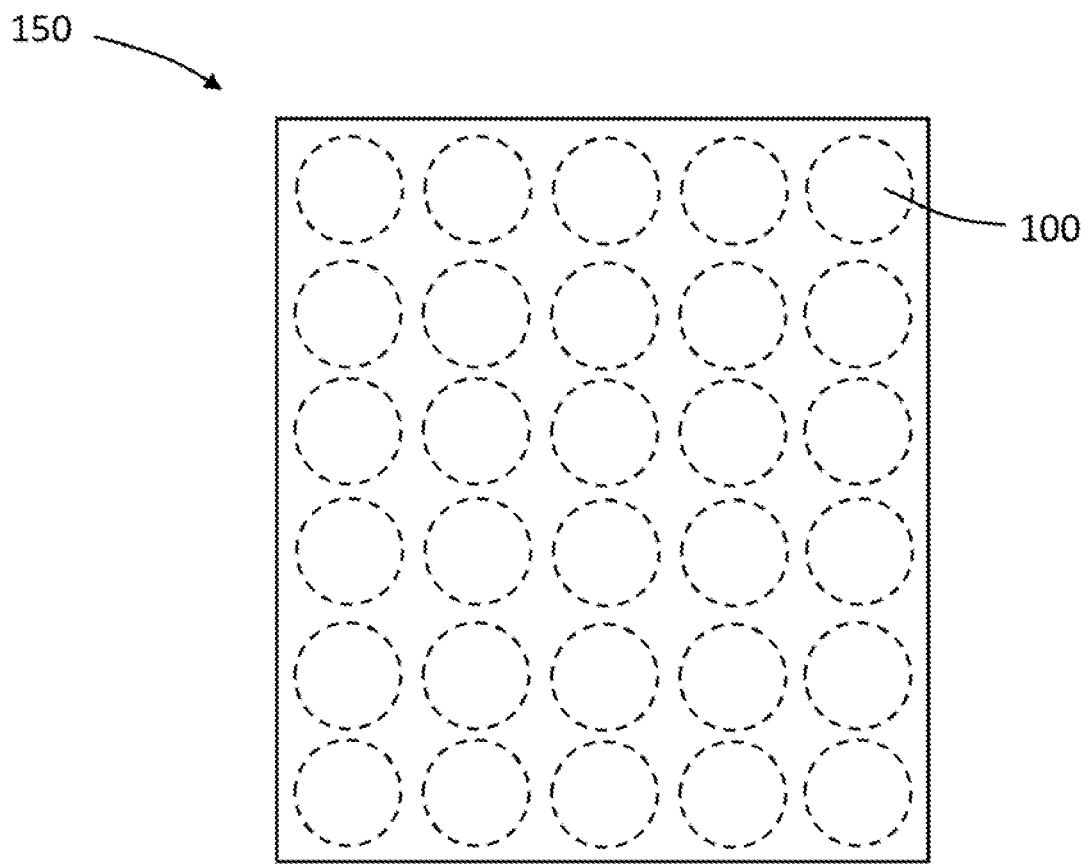
FIG. 2 is a schematic plan view of an embodiment of a sheet, from which patches may be formed.

Referring now to FIG. 2, a schematic plan view of a sheet 150, from which patches 100 may be formed, is shown. The patches 100 may be cut, punched, or the like, from the sheet 150. The patches 100 are indicated in dashed circles to indicate where the patches 100 may be cut, punched, or otherwise formed from the sheet 150. The sealing layer (not shown in FIG. 2) may be applied to a sheet of support material to form the sheet 150 from which the patches 100 may be formed.

The patch 150 may be affixed to a surface of a packaging film that may be used to form a package.

Figure 3:
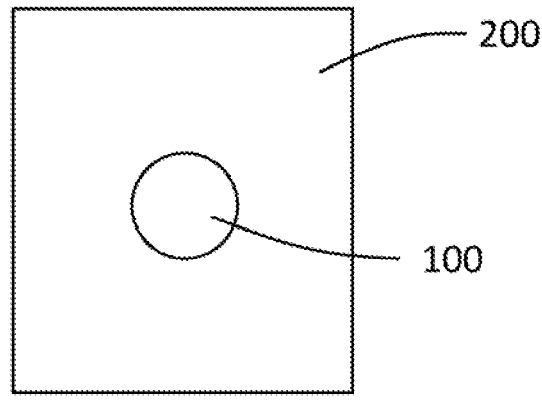
FIG. 3 is a schematic plan view of an embodiment of a patch affixed to a surface of an embodiment of a packaging film.

Referring now to FIG. 3, a schematic plan view of a patch 100 affixed to a surface of a packaging film 200 is shown. The packaging film 200 is transparent to ultraviolet radiation and is substantially impermeable to chlorine dioxide.

Figure 4:
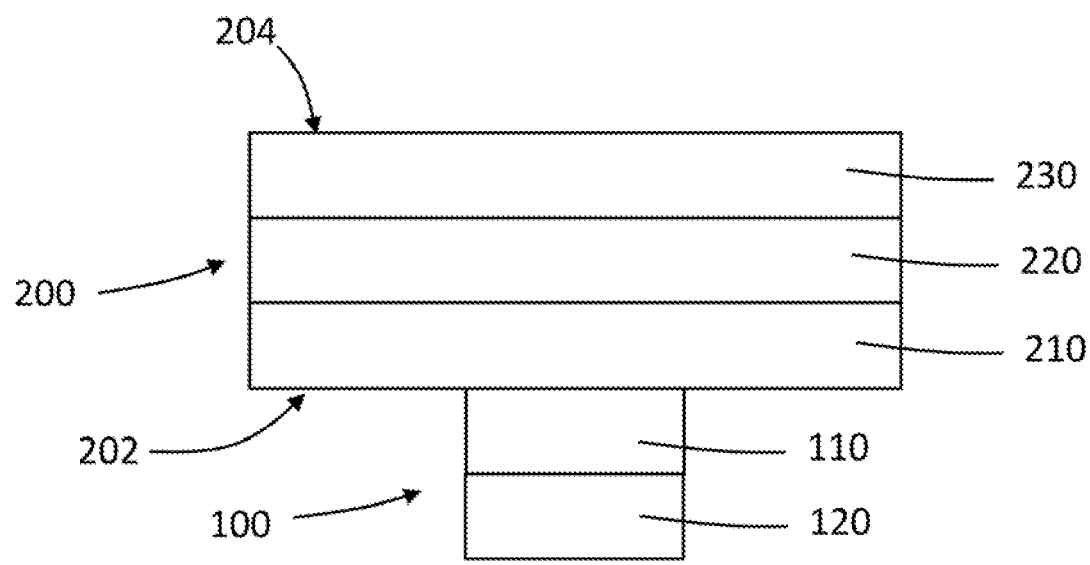
FIG. 4 is a schematic sectional view of an embodiment of a patch affixed to a surface of an embodiment of a packaging film.

Referring now to FIG. 4, a schematic sectional view of a patch 100 affixed to a first major surface 202 of a packaging film 200 is shown. The patch 100 comprises a sealing layer 110 comprising chlorite ions and a support 120 on which the sealing layer 110 is disposed. The patch 100 is affixed to the surface 202 of the packaging film 200 via the sealing layer 110. Surface 202 may form an interior surface of a package formed, at least in part by the packaging film 200. The depicted packaging film 200 is a multilayer film comprising a sealing layer 210, a barrier layer 220, and an abuse resistant outer layer 230 defining a second major surface 204 of the packaging film 200. The barrier layer 220 may be substantially impermeable to chlorine dioxide.

While the packaging film shown in FIG. 4 includes three layers, it will be understood that a suitable packaging film may have only a single layer or any suitable number or layers, provided that the film is transparent to ultraviolet light and substantially impermeable to chlorine dioxide.

The second major surface 204 of the packaging film 200 may form an exterior surface of a package formed, at least in part, by the packaging film 200.

Figure 5:
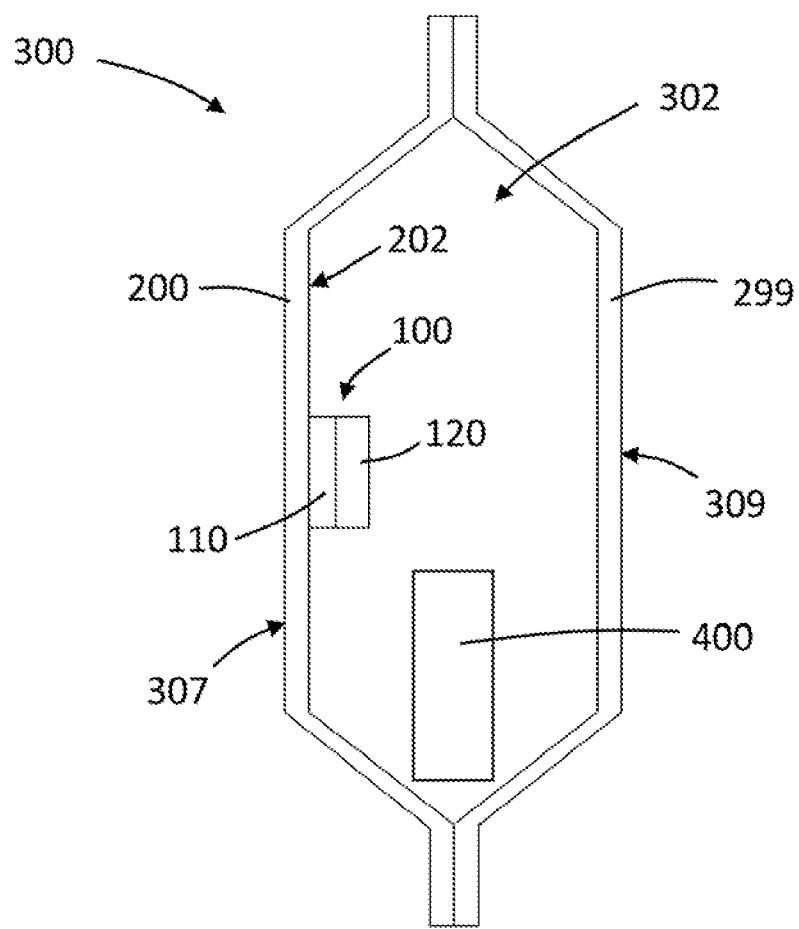
FIG. 5 is a schematic sectional view of an embodiment of a package.

Referring now to FIG. 5, a schematic sectional view of a package 300 is shown. The depicted package 300 is formed from a first packaging film 200 and a second packaging film 299, which may be made of the same or different materials. A patch 100 is affixed to a surface 202 of the first packaging film 200 that defines at least a portion of the interior space 302 of the package 300. The patch 100 comprises a support 120 and a sealing layer 110 comprising chlorite ions. The patch 100 is affixed to the surface 202 of the first packaging film 200 via the sealing layer 110. The support 120 is permeable to chlorine dioxide and is preferably opaque to ultraviolet light.

The first 200 and second 299 packaging films are transparent to ultraviolet light and are substantially impermeable to chlorine dioxide. The first packaging film 200 defines a first side 307 of the package 300, and the second packaging film 299 defines a second side 309 of the package 300.

An article 400 is disposed in the interior space 302 of the package 300. Ultraviolet light may be applied to the package 300 through the first side 307 to generate chlorine dioxide gas from chlorite ions in the sealing layer 110 of the patch 100. The generated chlorine dioxide may deodorize, disinfect, or sterilize the article 400.

Figure 6A:
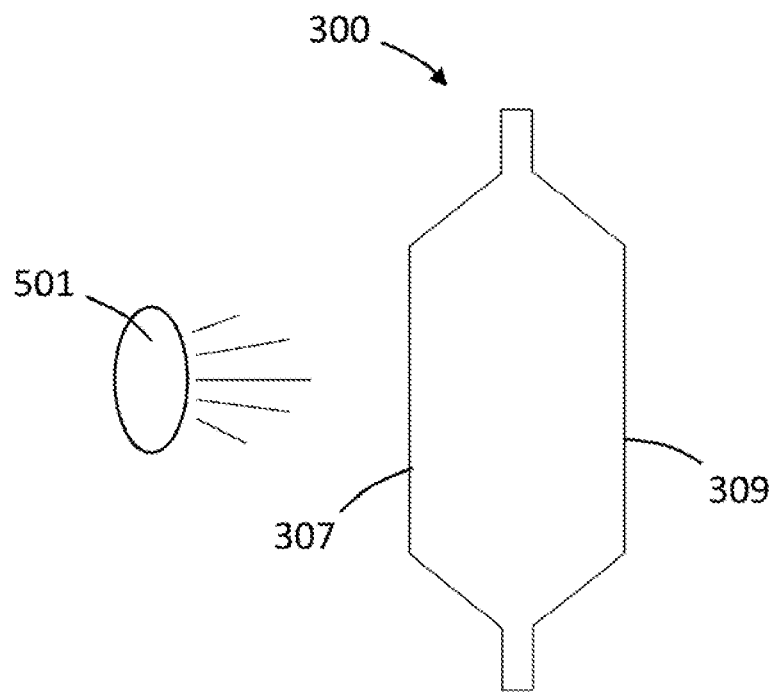
FIGS. 6A-B are schematic side views of an embodiment of a package exposed to ultraviolet light in accordance with an embodiment of a method.

Referring now to FIG. 6A, a schematic side view of a package 300 exposed to ultraviolet light from a UV source 501 is shown. The UV source 501 preferably emits ultraviolet light having a wavelength of about 254 nm and is positioned to expose a first side 307 of the package to the ultraviolet light. The package 300 may be a package depicted and described regarding FIG. 5. Accordingly, the ultraviolet light from the UV source 501 is transmitted through the first side 307 of the package to the sealing layer of the patch. Chlorite ions in the sealing layer of the patch are converted to chlorine dioxide in the presence of the ultraviolet light. The chlorine dioxide is released through the permeable support of the patch to the interior of the package 300. The ultraviolet light from the UV source 501 may be applied for a sufficient time for the chlorine dioxide levels in the interior of the package 300 to reach appropriate levels to, for example, deodorize, disinfect, or sterilize the article disposed in the interior of the package.

Figure 6B:
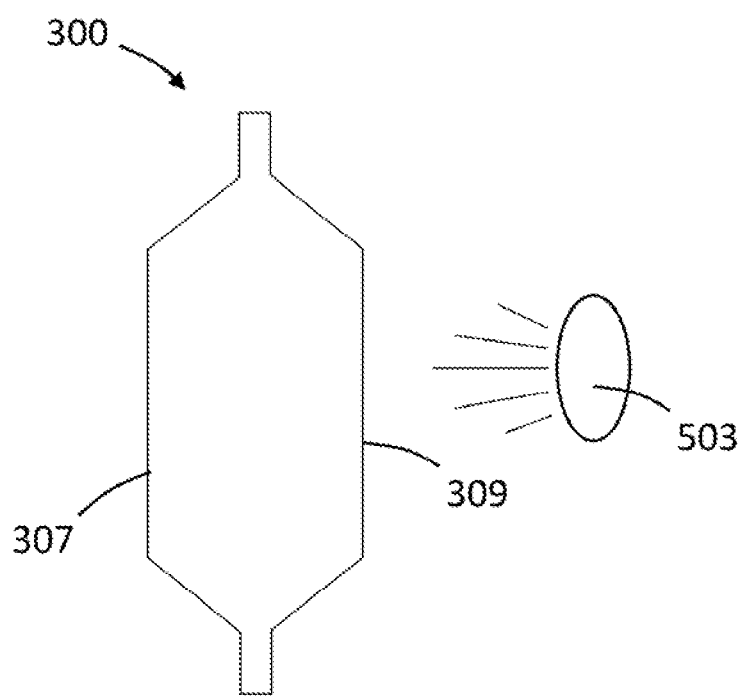

After a sufficient amount of time to accomplish the desired effect of the chlorine dioxide (e.g., deodorize, disinfect, or sterilize), the second side 309 of the package 300 may be exposed to ultraviolet light emitted from a second UV source 503 as depicted in FIG. 6B. The second UV source 503 preferably emits ultraviolet light having a wavelength in a range from about 300 nm to about 390 nm. Ultraviolet light from the second UV source 503 is transmitted through the second side 309 of the package 300, but is substantially blocked from reaching the sealing layer of the patch affixed to an inner surface of the first side 307 of the package 300 due to the opaque support of the patch. The ultraviolet light having the wavelength in a range from about 300 nm to about 390 nm may accelerate the degradation of the chlorine dioxide in the interior of the package 300.

Once the chlorine dioxide levels have reached sufficiently low levels inside the package 300 (e.g., below 0.5 ppm chlorine dioxide), the package may be safely opened. Sufficiently low levels of chlorine dioxide may be achieved relatively rapidly by applying the ultraviolet light having the wavelength in a range from about 300 nm to about 390 nm to the second side 309 of the package 300.

It is understood that this invention is not limited to the particular methodology, protocols, materials, and reagents described, as these may vary. It is also to be understood that the terminology used herein is for the purpose of describing particular embodiments only, and is not intended to limit the scope of the present invention.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein "a," "an," "the," "at least one," and "one or more" are used interchangeably. Thus, for example, a particle core that comprises "a" binder can be interpreted to mean that the particle core includes "one or more" binders. Similarly, a coating comprising "a" pore former can be interpreted to mean that the composition includes "one or more" pore formers.

As used herein, the term "or" is generally employed in its usual sense including "and/or" unless the content clearly dictates otherwise.

The term "and/or" means one or all of the listed elements or a combination of any two or more of the listed elements (e.g., preventing and/or treating an affliction means preventing, treating, or both preventing and treating an affliction).

Unless defined otherwise, all technical and scientific terms used herein have the same meanings as commonly understood by one of ordinary skill in the art to which this invention belongs. All publications and patents specifically mentioned herein are incorporated by reference for all purposes.

The following examples are offered for illustrative purposes only, and is not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

In this illustrative example, it is shown that patches having chlorine dioxide in a sealing layer may be affixed to an inner surface of a packaging film used to form a package and that chlorine dioxide may be generated from the chlorite ions in the sealing layer upon application of ultraviolet light. Heat Seal Coating Formulation Comprising Chlorite Ions A heat seal coating formulation needs to incorporate sufficient sodium chlorite for desired $ClO_2$ release levels while maintaining a stable dispersion. Table 1 provides an example of a heat seal coating formulation that meets the purpose. Dow HYPOD™ 8503 (polyolefin copolymer dispersion) is suitable as a base for a heat coating formulation. Keltrol AP serves as a viscosity modifier that thickens the coating to required levels. Surfynol 107L can be used as a defoaming agent. Formulations were prepared as indicated in Table 1 below.

TABLE 1

Heat seal coating formulations comprising chlorite ions

| No. | Material | Volume in ml | Mass in gram | Mass % In % | 3 gallon batch in kg |
|---|---|---|---|---|---|
| 1 | Dow HYPOD 8503 | 200 | 185 | 44.32 | 4.99 |
| 2 | Deionized water | 175 | 175 | 41.93 | 4.72 |
| 3 | Keltrol AP (xanthan gum) | — | 0.31 | 0.08 | 0.0075 (7.5 g) |

TABLE 1-continued

Heat seal coating formulations comprising chlorite ions

| No. | Material | Volume in ml | Mass in gram | Mass % In % | 3 gallon batch in kg |
|---|---|---|---|---|---|
| 4 | DuPont Headline 3875 | 45 | 56.025 | 13.64 | 1.54 |
| 5 | Air Products Surfynol 107L | 0.15 | 0.1425 | 0.03 | 0.0034 (3.4 g/3.59 ml) |
| | TOTAL | About 420 | 417.37 | 100 | 11.25 (approx.) |

By way of example, the 3 gallon batch of the heat seal coating formulation described in Table 1 above was prepared as follows. 3.6 mL of Surfynol 107L was mixed into 4.99 kg Dow HYPOD™ 8503, to which 1.72 kg deionized water was added. The resulting mixture was mixed for five minutes.

A master batch of 0.25% Keltrol AP was created in water first by mixing 7.5 g Keltrol AP in 3 kg deionized water for 1-2 hours with a high-shear mixer. The resulting water-based master batch was mixed into the Surfynol 107L/Dow HYPOD™ 8503 mixture, and 1.54 kg Headline 3875 was added slowly while mixing. The resulting composition was mixed for 15 minutes to produce a dispersion.

The dispersion remained stable for at least a day. Prior to use, the dispersion was mixed for at least 5 min with high-shear mixer.

Pressure Sensitive Adhesive Composition Comprising Chlorite Lens

Pressure sensitive adhesive compositions as indicated in Table 2 below were prepared.

TABLE 2

Pressure sensitive adhesive composition comprising chlorite ions

| No. | Material | Volume (ml) | Mass (g) | Mass % |
|---|---|---|---|---|
| 1 | Dow Robond PS-7860 | 50 | 50 | 72.4 |
| 2 | Deionized water | 4 | 4 | 6 |
| 4 | DuPont Headline 3875 | 12 | 15 | 21.5 |
| 5 | Air Products Surfynol 107L | 0.05 | 0.05 | 0.1 |
| | TOTAL | 66.05 | 69.05 | 100 |

The pressure sensitive adhesive compositions comprising chlorite ions were prepared as follows. The defoaming agent (107L) was mixed with the pressure sensitive adhesive (PS-7860) using a magnetic stirring bar. Sodium chlorite solution was added slowly to stirring solution along with deionized water. Stirring continues for 15 mins for thorough mixing.

Heat Seal Coating or PSA on TYVEK

The aqueous heat seal coating or PSA formulation can be applied to TYVEK or other non-woven material using a direct gravure coating process followed by thermal cure/drying. As an example, we coated TYVEK (grade: 1073B) with the heat seal coating comprising chlorite ions (5-10 lb/ream of dry coat-weight) using a direct gravure coater (Faustel Tech. Center, Milwaukee, WI) at 100 feet/min and a drying temperature of 150° F. (using a 60 ft. long oven). As an example, we coated TYVEK with the pressure sensitive adhesive formulation using drawdowns.

Alternatively, the coating may be applied using a flexo-press or an air-knife coater or any other suitable process. For example, the coating may be applied via mayer rod, offset, or reverse gravure coating processes, dipping, spraying, or the like.

Manufacturing of Packages Having 'Self-Sterilizing' Patches

The resulting 'self-sterilizing' heat seal patches were applied to packaging films that were formed into bags. The packaging films contained a layer of biaxially oriented polyamide (BOPA) and a multilayer, polyethylene (PE)-based layer. The PE-based layer served as a heat seal layer for forming the bag. The patches were applied to the PE layer.

Characterization of Packages Hating 'Self-Sterilizing Patches'

For all experiments, the bags were 8"×10" in size (BOPA/PE) and contained 2 self-sterilizing patches (6 cm diameter) sealed inside the package on one side. The patches were made of TYVEK 1073B coated with a heat seal formulation described above. The two patches had coat-weights of 7-8 lb/rm and 4-5 lb/rm, respectively.

The bags were moisturized by incubation in 'Jungle' chamber (40 C; 80% RH) for 1 hour. Alternatively, they could be moisturized by spraying water using a mist spray on top of the patch and incubating for an hour. They could also be moisturized by, for example, applying steam for 30 seconds, applying a wet cloth for 1 minute, applying a humidity control patch (BOVEDA) for 1 hour, or the like.

Figure 7:
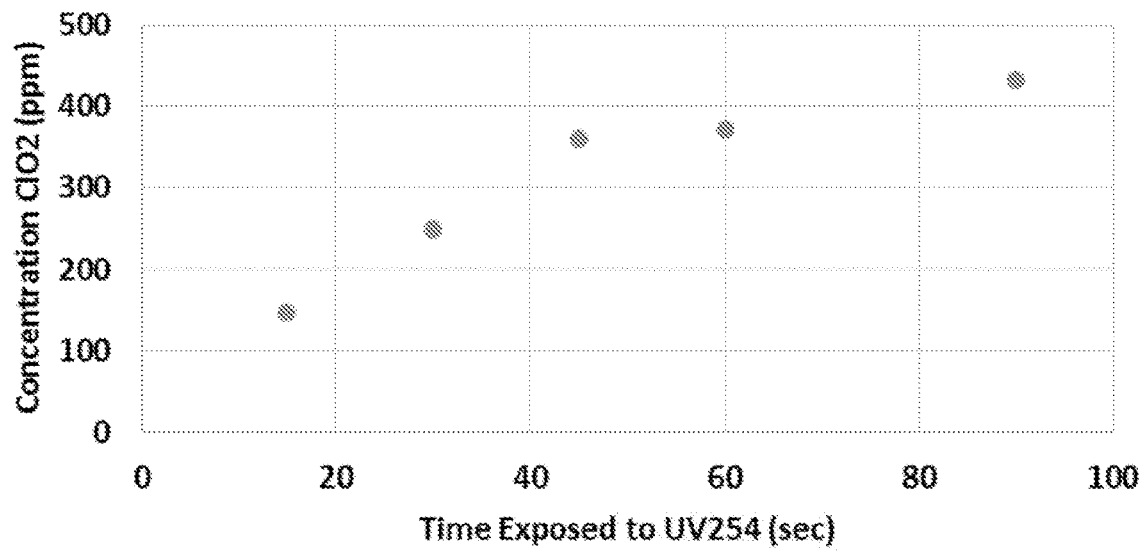
FIG. 7 is a graph showing chlorine dioxide release from a patch in a sealed package following exposure to ultraviolet light having a wavelength of 254 nm (UV254). Exposure to UV254 was done using XL-1500 UV crosslinker unit (contains six 16W UV254 bulbs) at a distance of 2" from the UV bulbs. The headspace of the packages (in the form of bags) was approx. 200 mL in volume. Data averaged from three replicates.
Figure 8:
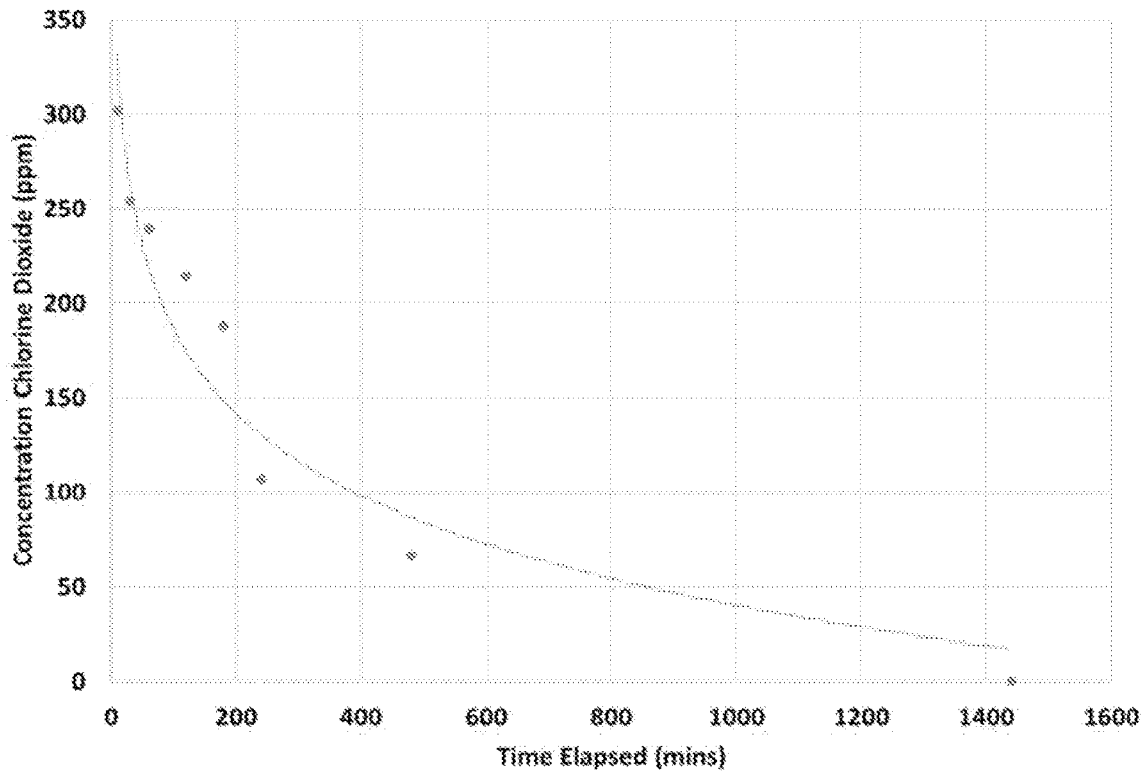
FIG. 8 is a graph of concentration of chlorine dioxide within package having a patch as a function of time. Three replicates per data point.

The amount of chorine dioxide generated following exposure to ultraviolet light having a wavelength of 254 nm (UV254) was determined. FIG. 7 shows nearly 400 ppm of $ClO_2$ could be generated within package after 60-90 seconds of UV exposure. FIG. 8 indicates $ClO_2$ concentration within packages goes essentially to zero within 24 hours.

Sterilization with 'Self-Sterilizing Patches'

Biological indicators (each consisting of $10^6$ *Geobacillus stearthermophilus* spores (#SCS-06; Crosstex Industries, Ohio)) were placed within self-sterilizing bags described above. Packages were sealed and $ClO_2$ was generated after UV activation (60 seconds). Biological indicators (BIs) were evaluated for sterilization after different times of incubation within packages to determine minimum time required for their sterilization. Bis were evaluated by incubating in media (Crosstex GMBCP-100; Incubation temperature: 55° C.) which changed color in response to bacterial growth. No change in color was observed if BIs incubated had been sterilized. Table 3 shows that BIs were sterilized within 2.5 hours of incubation within packages.

Package Barrier Towards $ClO_2$ Gas Released within

The ability of self-sterilizing bags to contain the $ClO_2$ that was released within was characterized as follows. Self-sterilizing bags that were sealed and triggered to released $ClO_2$ (concentration: 400 ppm in 200 mL) were stored within a secondary rigid container (hermetically closed; 3000 ml volume) along with a $ClO_2$ gas detector (Honeywell GasAlert Extreme; detection range: 0.01-1 ppm) that could detect any $ClO_2$ leak from the self-sterilizing bags and record it. The detector could record a minimum reading of 0.01 ppm of $ClO_2$. No $ClO_2$ was detected by the detector over 48 hours of storage indicating that any $ClO_2$ that may have escaped was less than <0.01 ppm in the volume of the container.

TABLE 3

Sterilization of BIs within bags

| Bag No. | Time elapsed after exposure to UV254 (hours) | Sterility |
|---|---|---|
| 1 | 2.5 | Sterile |
| 2 | 2.5 | Sterile |
| 3 | 2.5 | Sterile |
| 4 | 3 | Sterile |
| 5 | 3 | Sterile |
| 6 | 3 | Sterile |
| 7 | 24 | Sterile |
| 8 | 24 | Sterile |
| 9 | 24 | Sterile |

Example 2

In this illustrative example, it is demonstrated that exposure of self-sterilizing bags as described in EXAMPLE 1 (SS bags) to ultraviolet light having a wavelength of 365 nm (UV365) can accelerate the degradation of chlorine dioxide so that the bags may be safely opened substantially sooner than without exposure to UV365.

As indicated in EXAMPLE 1, for all experiments the bags were 8"×10" in size (BOPA/PE) and contained 2 self-sterilizing patches (6 mm diameter) sealed inside the package on one side. The two patches had coat-weights of 7-8 lb/rm and 4-5 lb/rm, respectively. The bags were moisturized by incubation in 'Jungle' chamber (40 C; 80% RH) for 1 hour.

Half-Life of $ClO_2$ within Package (without Using 365 nm Light)

In an experiment to characterize the half-life of $ClO_2$ within SS bags, the $ClO_2$ concentration within activated SS bags was measured at different time-points (3 replicates per time point) as described above in Example 1 (see. FIG. 8). The bags were activated by exposing the patch-containing side of SS bags to 254 nm UV light. As indicated in Example 1 above, FIG. 8 indicates $ClO_2$ concentration within packages goes to essentially zero within 24 hours due to the natural breakdown of $ClO_2$ evolved over time. Note that the concentration of $ClO_2$ at t=4 hr is ~100 ppm.

In another experiment, after UV activation at t=0 hr similar to above, the non-patch containing sides of the bags were exposed to UV365 at t=3 hr for different durations of time (1-10 min; 3 replicates each). The $ClO_2$ concentration within bags at t=4 hr was measured.

Figure 9:
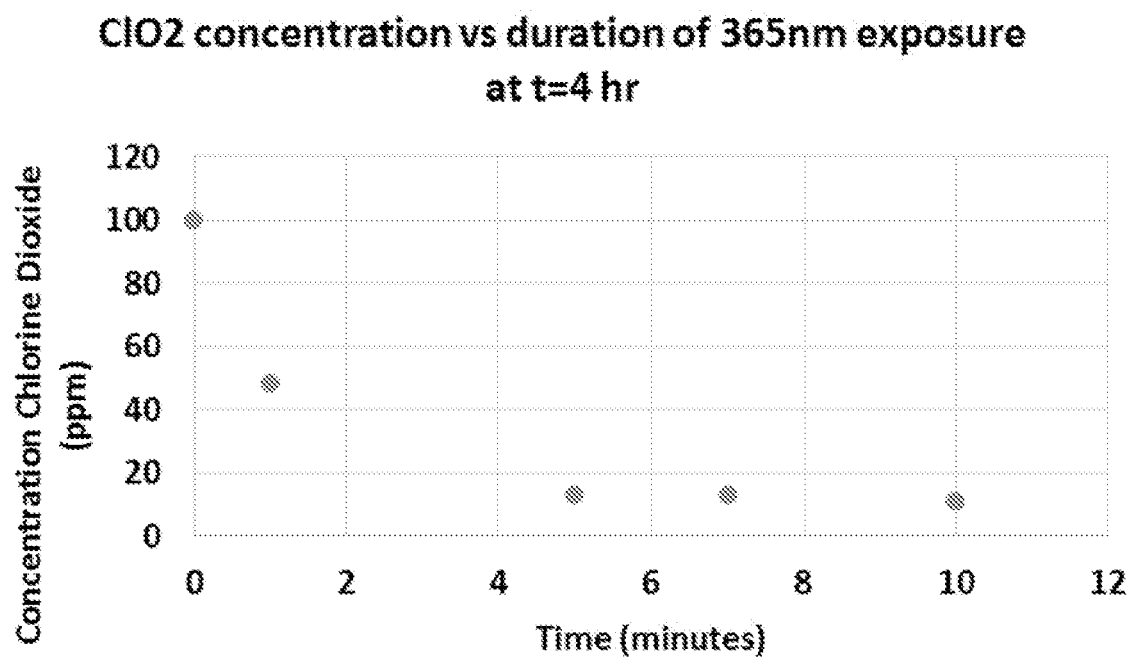
FIG. 9 is a graph of chlorine dioxide concentration in a package having a patch verses duration of exposure to ultraviolet light having a wavelength of 365 nm.

FIG. 9 shows that SS bags exposed to UV365 for 10 min had 10 ppm of $ClO_2$ gas at t=4 hr as opposed to 100 ppm for bags not exposed to UV365.

Note that UV365 can also generate $ClO_2$ gas from $NaClO_2$, albeit in smaller quantities than UV254. However, the design of the package prevents the UV365 from re-activating $ClO_2$ release since the TYVEK patch is opaque to UV light and the heat seal coating containing $NaClO_2$ is not accessible to UV light from the other side. When the package was subjected to UV365 from the wrong side (i.e., the same side as the UV254), the concentration of $ClO_2$ remaining in the bag was found to be about 5 ppm higher than when the package was subjected to UV 365 from the correct side (i.e., the opposite as the UV254) (data not shown).

What is claimed is:

1. A film having first and second major surfaces, comprising:
   a support that is permeable to chlorine dioxide and that defines the first major surface of the film, wherein the support consists of a non-woven material comprising polyethylene fibers; and
   a sealing layer comprising chlorite ions, wherein the sealing layer is in direct contact with the support and defines the second major surface of the film, and wherein the sealing layer is configured to affix the film to another structure.

2. The film of claim 1, wherein the support comprises one or more layers.

3. The film of claim 1, wherein the support is opaque to ultraviolet light having a wavelength in a range from about 300 nm to about 390 nm.

4. The film of claim 1, wherein the polyethylene fibers comprise high-density polyethylene fibers.

5. The film of claim 1, wherein the sealing layer comprises a heat sealable polymeric composition.

6. The film of claim 1, wherein the sealing layer comprises a pressure sensitive adhesive.

7. The film of claim 1, wherein the chlorite ions are present in the sealing layer at a concentration from about 0.1 wt. % to about 70 wt. %.

8. The film of claim 1, wherein the film is in the form of a sheet.

9. The film of claim 1, wherein the film is in the form of a patch.

10. A package comprising:
    a packaging film having an inner surface defining at least a portion of an interior space of the package for housing an article, wherein the packaging film is substantially impermeable to chlorine dioxide; and
    the film in the form of the patch of claim 9, wherein the patch is affixed to the inner surface of the packaging film by the sealing layer, and
    wherein the packaging film is transparent to ultraviolet light having a wavelength of about 254 nm in a portion to which the patch is affixed to the packaging film.

11. A method comprising:
    providing a package according to claim 10; and
    subjecting the package to ultraviolet light having a wavelength of about 254 nm to generate chlorine dioxide from the chlorite ions in the sealing layer of the patch.

12. The method of claim 11, wherein the package is subjected to a sufficient amount of the ultraviolet light to result in a concentration of chlorine dioxide in the interior space of at least about 10 ppm.

13. The method of claim 11, wherein the package comprises a first side and a second side opposing the first side, and wherein the packaging film having the inner surface to which the patch is affixed defines the first side of the package, and wherein (i) a second packaging film defines the second side of the package or (ii) a portion of the first packaging film, in a region to which the patch is not affixed, forms the second side of the package, and wherein the ultraviolet light is applied from a location exterior to the package on the first side towards the inner surface of the packaging film to which the patch is affixed.

14. The method of claim 13, wherein at least the second side of the package is transparent to ultraviolet light having a wavelength from about 300 nm to about 390 nm and the patch is opaque to ultraviolet light having a wavelength from about 300 nm to about 390 nm, and wherein the method further comprises subjecting the package to ultraviolet light having a wavelength from about 300 nm to about 390 nm which is applied from a location exterior to the package on the second side such that the opaque patch prevents a substantial amount of the ultraviolet light having the wavelength from about 300 nm to about 390 nm from reaching the sealing layer comprising the chlorite ions, wherein the ultraviolet light having the wavelength from about 300 nm to about 390 nm accelerates the degradation of the generated chlorine dioxide.

15. The method of claim 13, wherein at least the second side of the package is transparent to ultraviolet light having a wavelength of about 365 nm and the patch is opaque to ultraviolet light having a wavelength of about 365 nm, and wherein the method further comprises subjecting the package to ultraviolet light having a wavelength of about 365 nm which is applied from a location exterior to the package on the second side such that the opaque patch prevents a substantial amount of the ultraviolet light having the wavelength of about 365 nm from reaching the sealing layer comprising the chlorite ions, wherein the ultraviolet light having the wavelength of about 365 nm accelerates the degradation of the generated chlorine dioxide.

16. The method of claim 13, wherein at least the second side of the package is transparent to ultraviolet light having a wavelength of about 312 nm and the patch is opaque to ultraviolet light having a wavelength of about 312 nm, and wherein the method further comprises subjecting the package to ultraviolet light having a wavelength of about 365 nm which is applied from a location exterior to the package on the second side such that the opaque patch prevents a substantial amount of the ultraviolet light having the wavelength of about 312 nm from reaching the sealing layer comprising the chlorite ions, wherein the ultraviolet light having the wavelength of about 312 nm accelerates the degradation of the generated chlorine dioxide.

17. The package of claim 10, wherein the support is opaque to ultraviolet light having a wavelength in a range from about 300 nm to about 390 nm.

18. The film of claim 1, wherein the support is opaque to ultraviolet light having a wavelength of about 365 nm.

19. The film of claim 1, wherein the support is opaque to ultraviolet light having a wavelength of about 312 nm.

\* \* \* \* \*

UNITED STATES PATENT AND TRADEMARK OFFICE
CERTIFICATE OF CORRECTION

PATENT NO. : 12,084,601 B2
APPLICATION NO. : 16/957231
DATED : September 10, 2024
INVENTOR(S) : Rishabh Jain and Claire E. Kalb It is certified that error appears in the above-identified patent and that said Letters Patent is hereby corrected as shown below:

In the Specification

Column 5, Line 24 Delete "5%" and insert -- 15% --, therefor.

Column 5, Line 66 Delete "55-6" and insert -- 55-60 --, therefor.

Column 12, Line 1 Delete "mis" and insert -- mils --, therefor.

Column 15, Line 26 Delete "run" and insert -- nm --, therefor.

Column 19, Table 1-continued, under Mass in gram (Column 4) Delete "56.025" and insert -- 56.925 --, therefor.

Column 19, Line 33 Delete "Lens" and insert -- ions --, therefor.

Column 20, Line 14 Delete "Hating" and insert -- Having --, therefor.

Signed and Sealed this
Twenty-sixth Day of August, 2025

Coke Morgan Stewart
*Acting Director of the United States Patent and Trademark Office*